(12) United States Patent
Beckman (10) Patent No.: US 11,627,986 B2
(45) Date of Patent: Apr. 18, 2023

(54) TROCAR SUPPORT

(71) Applicant: Ethicon LLC, Guaynabo, PR (US)

(72) Inventor: Andrew Beckman, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 137 days.

(21) Appl. No.: 17/062,667

(22) Filed: Oct. 5, 2020

(65) Prior Publication Data
US 2021/0161559 A1 Jun. 3, 2021

Related U.S. Application Data

(60) Continuation of application No. 16/226,316, filed on Dec. 19, 2018, now Pat. No. 10,792,070, which is a division of application No. 15/380,572, filed on Dec. 15, 2016, now Pat. No. 10,238,422.

(51) Int. Cl.
| | |
|---|---|
| *A61B 17/34* | (2006.01) |
| *A61B 90/50* | (2016.01) |
| *A61B 34/30* | (2016.01) |
| *A61M 39/04* | (2006.01) |
| *A61B 17/00* | (2006.01) |

(52) U.S. Cl.
CPC ...... *A61B 17/3474* (2013.01); *A61B 17/3421* (2013.01); *A61B 17/3498* (2013.01); *A61B 34/30* (2016.02); *A61B 90/50* (2016.02); *A61M 39/04* (2013.01); *A61B 2017/00477* (2013.01); *A61B 2017/3492* (2013.01)

(58) Field of Classification Search
CPC ... A61B 34/30; A61B 90/50; A61B 2034/304; A61B 17/34; A61M 39/04; A61M 2039/0626; A61M 2039/0673

USPC .................................................. 604/167.06
See application file for complete search history.

(56) References Cited

U.S. PATENT DOCUMENTS

| | | | |
|---|---|---|---|
| 8,114,345 B2 | 2/2012 | Dlugos, Jr. et al. | |
| 10,238,422 B2 | 3/2019 | Beckman | |
| 10,792,070 B2 * | 10/2020 | Beckman ........... | A61B 17/3498 |
| 2006/0161136 A1 | 7/2006 | Anderson et al. | |
| 2014/0171855 A1 | 6/2014 | Mastri et al. | |
| 2018/0168689 A1 | 6/2018 | Beckman | |

(Continued)

FOREIGN PATENT DOCUMENTS

| | | |
|---|---|---|
| EP | 2338425 A1 | 6/2011 |
| WO | 2014/151621 A1 | 9/2014 |

OTHER PUBLICATIONS

U.S. Appl. No. 15/380,572, filed Dec. 15, 2016, Trocar Support.

(Continued)

*Primary Examiner* — Deanna K Hall
(74) *Attorney, Agent, or Firm* — Mintz Levin Cohn Ferris Glovsky and Popeo, P.C.

(57) ABSTRACT

Various trocars and trocar supports are provided for allowing an insufflation port on the trocar to be coupled through the trocar support to an insufflation fluid. In one embodiment, the trocar includes a housing, a cannula extending through the housing, and an insufflation port projecting from the housing. A trocar support is provided having an opening that receives the insufflation port on the housing such that the insufflation port is unobtrusive during use and can be connected and disconnected rapidly.

13 Claims, 4 Drawing Sheets

(56) References Cited

U.S. PATENT DOCUMENTS

2019/0125405 A1   5/2019   Beckman

OTHER PUBLICATIONS

U.S. Appl. No. 16/226,316, filed Dec. 19, 2018, Trocar Support.
International Search Report and Written Opinion for International Applicaion No. PCT/IB2017/057457, dated Feb. 7, 2018, 11 pages.

* cited by examiner

TROCAR SUPPORT

CROSS-REFERENCE TO RELATED APPLICATIONS

This application is a continuation of U.S. application Ser. No. 16/266,316 filed on Dec. 19, 2018 and entitled "Trocar Support," which is a divisional of U.S. application Ser. No. 15/380,572 (now U.S. Pat. No. 10,238,422) filed on Dec. 15, 2016 and entitled "Trocar Support," which are hereby incorporated by reference in their entireties.

FIELD

Methods and devices are provided for mounting a trocar on a surgical robotic arm.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Various surgical tools and methods are provided for mounting a trocar onto a trocar support.

In one embodiment, a surgical system is provided and includes a trocar having a housing and a cannula extending distally from the housing. The housing and the cannula can define a tool pathway extending therethrough for receiving a tool. The housing can include at least one seal configured to form a seal across the tool pathway and an insufflation port extending from the housing and in fluid communication with the tool pathway for delivering insufflation therethrough. The system can also include a carrier configured to be mounted on a distal end of a surgical robotic arm. The carrier can include an elongate member having a trocar support on a distal end thereof. The trocar support can be configured to support the trocar in a substantially fixed position, and at least one of the elongate member and the trocar support can include an opening formed therein for receiving the insufflation port on the trocar.

In one embodiment, the insufflation port can be concealed by the opening. In certain embodiments, the trocar support can extend substantially perpendicular to the elongate member. In other aspects, the opening extends through each of the trocar support and the elongate member.

In another embodiment, the trocar support can include first and second movable arms that are configured to engage the housing of the trocar therebetween. The housing of the trocar can include opposed grooves formed therein for seating the first and second movable arms. The opening can be positioned between the first and second movable arms and can be configured to receive the insufflation port on the trocar.

In another embodiment, the opening can be a cut-out formed in a distal end of the elongate member. In other aspects, the insufflation port can extend substantially parallel to the cannula, and the opening can be formed in an upper surface of the trocar support for receiving the insufflation port. Coupling of the insufflation port to the opening can mate the trocar to the trocar support for holding the trocar in a substantially fixed position. In other aspects, the insufflation port can extend substantially perpendicular to the cannula, and the opening can be formed in a terminal end of the trocar support and is in communication with a pathway extending through the elongate member. In certain embodiments, the insufflation port can include a Bal-Seal.

A robotic system is also provided and in one embodiment the system can include a trocar having a housing, a cannula extending from the housing, a tool pathway extending through the housing and the cannula, and an insufflation port projected from the housing and in fluid communication with the tool pathway. The system can also include an electromechanical robotic arm configured to mount to a support and a carrier mounted to a distal end of the robotic arm. The carrier can include a trocar support having an opening formed therein for receiving at least a portion of the insufflation port on the trocar.

In one embodiment, the trocar support can include a recess formed therein for seating the housing on the trocar. In other aspects, the trocar can be configured to be fixedly mounted to the trocar support when the insufflation port is inserted into the opening. In another embodiment, the insufflation port can extend substantially perpendicular to the cannula, and the opening can be formed in an upper surface of the trocar support for receiving the insufflation port.

Surgical methods are also provided and in one embodiment the method can include inserting an insufflation port on a trocar into a bore in a trocar holder mounted on a distal end of a surgical robotic arm, delivering an insufflation fluid through the bore into the insufflation port in the trocar such that the insufflation fluid travels through a tool pathway extending through the trocar and is delivered into a body cavity of a patient, and inserting a tool through the tool pathway of the trocar to position an end effector on a distal end of the tool within the body cavity.

The insufflation port can be prevented from rotating relative to the trocar holder. In certain aspects, inserting the insufflation port into the bore in the trocar holder can mate the trocar to the trocar holder.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Additionally, WIPO Patent Publication No. WO2014/151621, filed on Mar. 13, 2014 and entitled "Hyperdexterous Surgical System," is incorporated herein by reference.

Various surgical tools and methods are provided for mounting a trocar to a surgical robotic arm. A trocar generally has a housing and a cannula extending from the housing with a tool pathway extending through the housing and the cannula for receiving a surgical tool. At least one seal is formed across the tool pathway for sealing the tool pathway when no instrument is present and when an instrument is present. The housing has an insufflation port that is in fluid communication with the tool pathway for delivering insufflation therethrough and into a body cavity.

In robotic surgery, a trocar is mounted to a carrier on the distal end of a surgical robotic arm, and the trocar provides a pathway through tissue for a surgical tool coupled to the robotic arm. Depending on the location of an insufflation port, care may be required to avoid damaging the insufflation port when connecting the trocar to the surgical robotic arm and when connecting insufflation tubing to the stopcock and/or the insufflation port. In many trocars, the insufflation port has a high profile and takes up a lot of space during minimally-invasive surgery. As a result, the insufflation port can interfere with positioning of the trocar, e.g. by hitting the skin surface and/or by hitting other tools and/or other surgical robotic arms. Thus a trocar support is provided that is mounted on a distal end of a surgical robotic arm, and insufflation can be delivered through the trocar support directly to the trocar to reduce the space requirements of the trocar, and thereby prevent interference during use.

Figure 1:
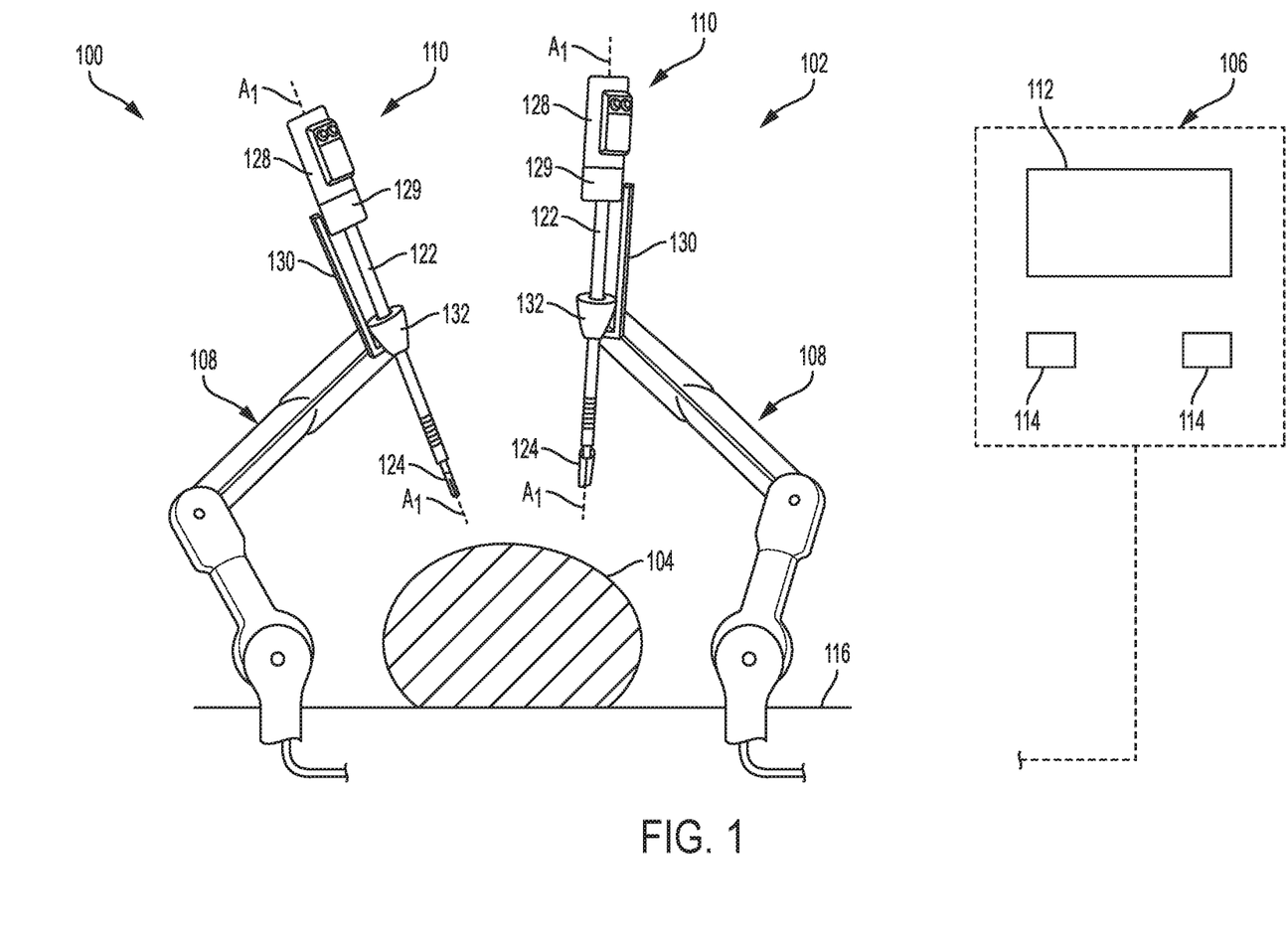
FIG. 1 is a perspective view of one embodiment of a surgical robotic system that includes a patient-side portion and a user-side portion.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure.

The patient-side portion 102 can have a variety of configurations. As illustrated in FIG. 1, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1). Alternatively, the patient-side portion 102 can include a single assembly that includes one or more robotic arms 108 extending therefrom.

The surgical tool 110 includes an elongate shaft 122, an end effector 124, and a tool housing 128 coupled to a proximal end of the shaft 122. The shaft 122 can have any of a variety of configurations. In general, the shaft 122 is an elongate member extending distally from the housing 128 and having at least one inner lumen extending therethrough. The shaft 122 is fixed to the housing 128, but in other embodiments the shaft 122 can be releasably coupled to the housing 128 such that the shaft 122 can be interchangeable with other shafts. This may allow a single housing 128 to be adaptable to various shafts having different end effectors. The end effector 124 can also have a variety of sizes, shapes, and configurations. The end effector 124 can be configured to move relative to the shaft 122, e.g., by rotating and/or articulating, to position the end effector 124 at a desired location relative to a surgical site during use of the tool 110. The housing 128 includes various components (e.g., gears and/or actuators) configured to control the operation various features associated with the end effector 124 (e.g., any one or more of clamping, firing, rotation, articulation, energy delivery, etc.). In at least some embodiments, as in this illustrated embodiment, the surgical tool 110 is configured to releasably couple to a tool driver 129 mounted on a carrier 130 on the distal end of the robotic arm 108, and the tool housing 128 can include coupling features configured to allow the releasable coupling of the tool 110 to the robotic arm 108. As further shown in FIG. 1, the carrier 130 can include a trocar or trocar support 132 mounted thereon for receiving the shaft 122 of the tool 110 therethrough. A person skilled in the art will appreciate that the surgical tool 110 can have any of a variety of configurations, and it can be configured to perform at least one surgical function. The surgical tool can be, for example, a stapler, a clip applier, forceps, a grasper, a needle driver, scissors, an electrocautery tool that applies energy, a suction tool, an irrigation tool, an imaging device (e.g., an endoscope or ultrasonic probe), etc.

The control system 114 can have a variety of configurations and can be located adjacent to the patient e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and surgical tools 110.

As indicated above, in an exemplary embodiment a trocar is provided with a housing and a cannula having a tool pathway extending therethrough to receive an elongate shaft and an end effector of a surgical tool, such as the surgical tool 110. A variety of different mechanisms can be used to connect an insufflation pathway to the trocar such that the insufflation pathway and/or any stopcock are unobtrusive during use and can be connected and disconnected rapidly.

Figure 2:
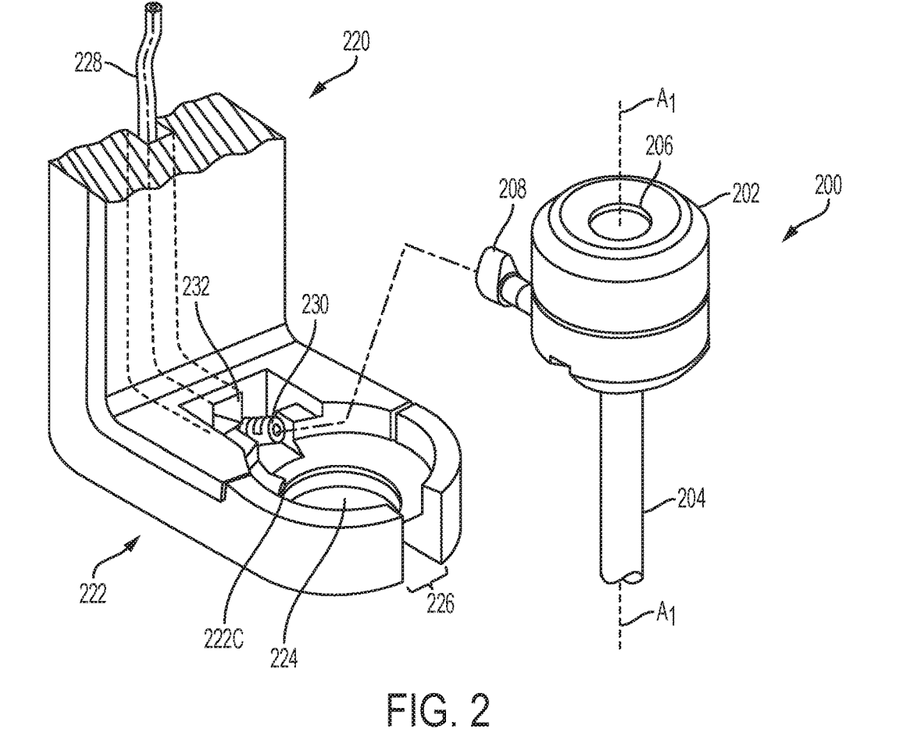
FIG. 2 is a perspective view of one embodiment of a trocar and a trocar support.

FIG. 2 illustrates one embodiment of a trocar 200 with a housing 202 and a cannula 204. A tool pathway extends through an opening 206 in the housing 202 and through the cannula 204 along a longitudinal axis A1. To facilitate viewing within a body cavity, insufflation fluid can be introduced through an insufflation port 208 in the trocar 200 to inflate the body cavity. The insufflation port 208 extends outward from a sidewall of the housing, substantially perpendicular to the axis A1. The insufflation port can be in the form of a hollow protrusion or tube, and it can differ from prior art insufflation ports in that no stopcock is required. The insufflation port 208 is in fluid communication with the pathway extending through the trocar 200 and into a body cavity of a patient, such that insufflation can be delivered into the port and through the trocar cannula into a body cavity.

In order to prevent leakage from the trocar 200 when filling the body cavity with insufflation fluid, the trocar can include one or more seals extending across the tool pathway. For example, the trocar can include a zero-closure valve, which seals the tool pathway when no tool present, and/or an instrument seal, which forms a seal around the shaft of an instrument passed therethrough. A person skilled in the art will appreciate that any seal(s) known in the art can be used to form a seal across the tool pathway in the trocar.

As further shown in FIG. 2, a robotic arm 220 is provided that has a trocar support 222 mounted on its distal end that receives and provides support to the trocar 200. In general, the robotic arm 220 has a generally elongate configuration and the trocar support extends substantially perpendicular from a distal end of the robotic arm 220. In various embodiments, the trocar support can be pivotably connected to the robotic arm and can pivot about the arm. The trocar support 222 has an opening 224 formed therein and a gap 226 extending into the opening 224. The gap 226 is wide enough to allow a trocar cannula 204 to pass therethrough, and the opening 224 is large enough to allow the distalmost end of the trocar housing 202 to be seated therein without passing therethrough. The trocar support 222 forms a cradle 222c around the opening 224, that functions to receive and cradle the bottom surface of the trocar housing while allowing passage of the cannula into the body cavity of a patient while. The robotic arm 220 has an insufflation pathway formed therein and extending along any portion of the length thereof. The pathway can extend across the trocar support 222, terminating at a location proximally adjacent to the opening 224 in the trocar support 222. In the illustrated embodiment, an insufflation tubing 228 extends through the insufflation pathway, however in other aspects the insufflation pathway can function to directly transport insufflation fluid. The insufflation tubing 228 includes a port 230 on a terminal end thereof that is seated in a bore 232 formed in the trocar support 222. The port 230 can be positioned to couple with the port 208 on a trocar when a trocar is seated in the opening 224.

In use, when port 208 is connected to port 230, the insufflation tubing 228 can deliver an insufflation fluid therethrough and into the trocar for delivery to a body cavity. When the trocar 200 is placed in the trocar support 222, the insufflation port 208 can extend toward or into the bore 232, preventing port 208, port 230, and the insufflation tubing 228 from interfering with use of the device. In some embodiments, turning on and off insufflation (e.g. flow control) can be accomplished via a flow control valve placed anywhere in line with the tubing 228 routed through or along the robotic arm 220. User control of the flow control value can be accomplished either manually (e.g. mechanically at the source) and/or remotely (e.g. automatic activation) via a user interface, such as the user-side portion 106 or other user consoles. In other embodiments, the insufflation port can be concealed in the trocar by a hinged insufflation lock. As the trocar is connected to a trocar support on a robotic arm, the hinged insufflation lock can rotate to expose the insufflation port on the trocar to the corresponding insufflation connection on the robotic arm. Alternatively an insufflation port can extend out of a bottom of the trocar.

Figure 3:
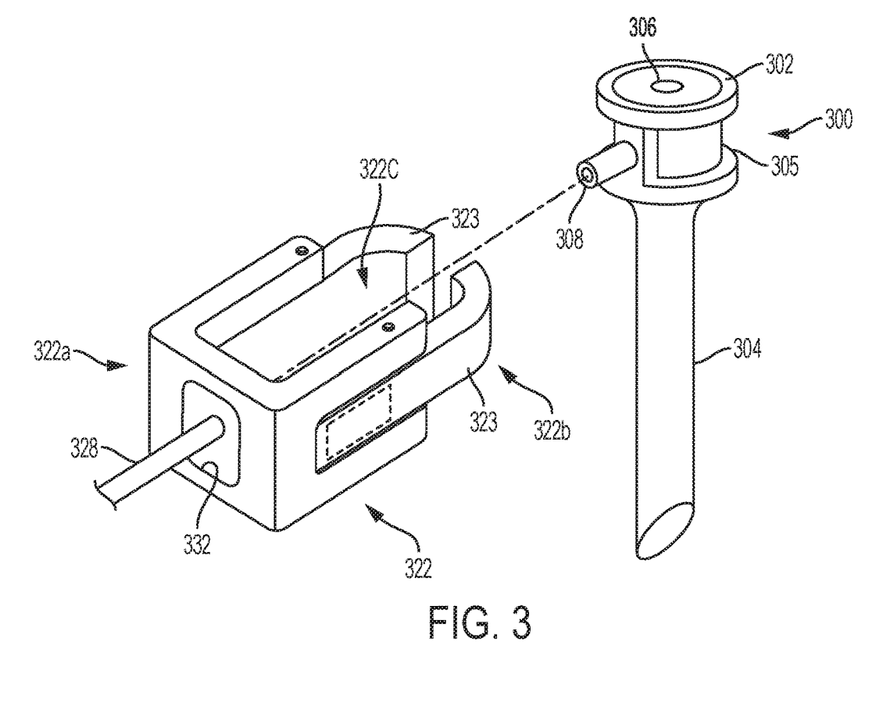
FIG. 3 is a perspective view of another embodiment of a trocar connecting to a surgical robotic arm.

FIG. 3 illustrates another embodiment of a trocar 300 similar to the trocar 200 of FIG. 2. The trocar 300 has a housing 302 and a cannula 304 with a tool pathway running therethrough and at least one seal extending thereacross, as discussed above. The proximal end of the housing 302 includes an opening 306 for receiving a surgical tool, and an insufflation port 308 extends outward from a sidewall of the housing 302. The port 308 is in fluid communication with the tool pathway extending through the trocar 300 such that fluid can be delivered through the port 308 and into a body cavity of a patient. FIG. 3 further illustrates a trocar support 322 that can be formed on or mounted on a distal end of a robotic arm. In this embodiment, the trocar support 322 has a generally U-shaped configuration with a first end 322a that mounts to the robotic arm and a second opposite end 322b that is configured to receive the trocar therein. As shown, the first end 322a has an opening 332 formed therein with an insufflation tubing 328 extending through the opening 332. The insufflation tubing 328 is configured to connect to the port 308 on the trocar 300. The second end 322b of the trocar support 322 opposed arms 323 that define an opening therebetween for receiving the trocar, and the inner surface of the arms 323 define a cradle 322c therein for engaging the trocar housing. The arms 323 of the trocar support 322 can be biased radially inward by a spring mechanism in the trocar support 322. The arms 323 can be moved radially outward by overcoming the spring bias to allow the trocar 300 to be inserted into the cradle 322c. When the arms are released, the spring bias causes the arms to close around the trocar support 322 and grip the trocar 300 within the trocar support 322. As shown in FIG. 3, the trocar housing can include at least one groove 305 formed therein for seating the arms so as to prevent sliding of the trocar housing 302 relative to the trocar support 322.

In use, when the insufflation tubing 328 is connected to the port 308 and the trocar 300 is placed in the trocar support 322, the insufflation tubing 328 and the port 308 will be concealed within the trocar support 322, and insufflation can be provided to a body cavity through the insufflation tubing 328 and the trocar. In some embodiments, insufflation flow can be controlled by a flow control valve placed anywhere in line with the tubing 328 routed through or along the robotic arm 220. User control of the flow control value can be accomplished either manually (e.g. mechanically at the source) and/or remotely (e.g. automatic activation) via a user interface, such as the user-side portion 106 or other user consoles.

Figure 4:
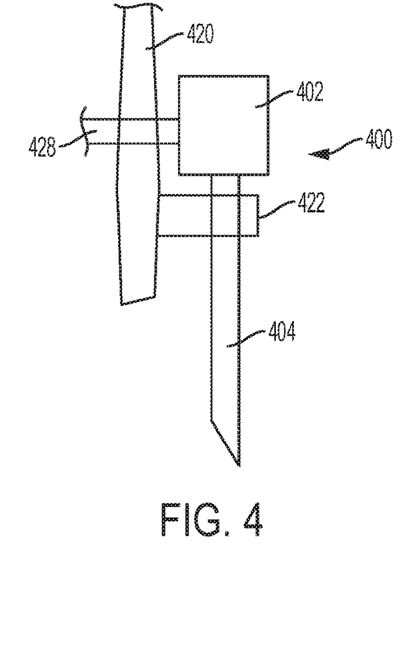
FIG. 4 is a cross-sectional view of another embodiment of a trocar connecting to a surgical robotic arm.
Figure 5:
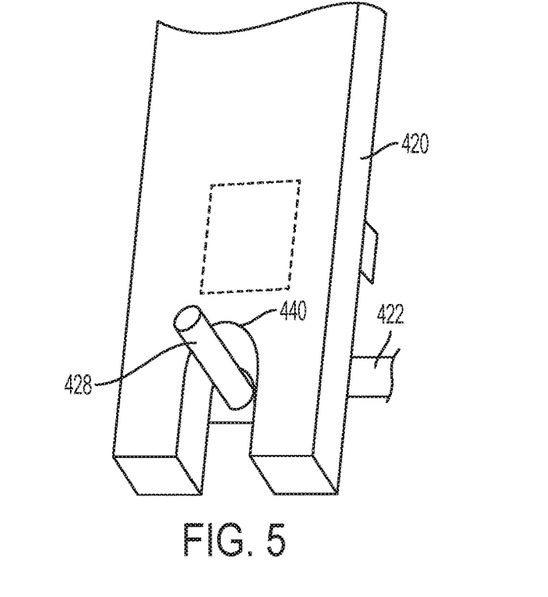
FIG. 5 is a perspective view from behind the surgical robotic arm of FIG. 4.

FIGS. 4 and 5 illustrate another embodiment of a trocar 400 that is similar to trocar 200 and that includes a housing 402 and a cannula 404 as described above. The trocar 400 is configured to mount to a trocar support 422 formed on or mounted on a distal end of a carrier 420, such as a robotic arm. In this embodiment, the carrier 420 is in the form of a generally elongate body having a cut-out or opening 440 formed in a distal end thereof for receiving an insufflation tubing 428 or for receiving a port on the trocar 400. The support 422 can extend outward from the carrier 420, e.g., substantially perpendicular to the carrier, and it can be configured to receive the trocar 400 therethrough, e.g., using techniques discussed above. The port or insufflation tubing 428 can be coupled to an insufflation source so as to allow an insufflation fluid to be delivered into the trocar and into a body cavity of a patient. With the port or tubing positioned within the cut-out, the port will remain out of the way and thus will not interfere with use of the trocar during robotic surgery.

Figure 6:
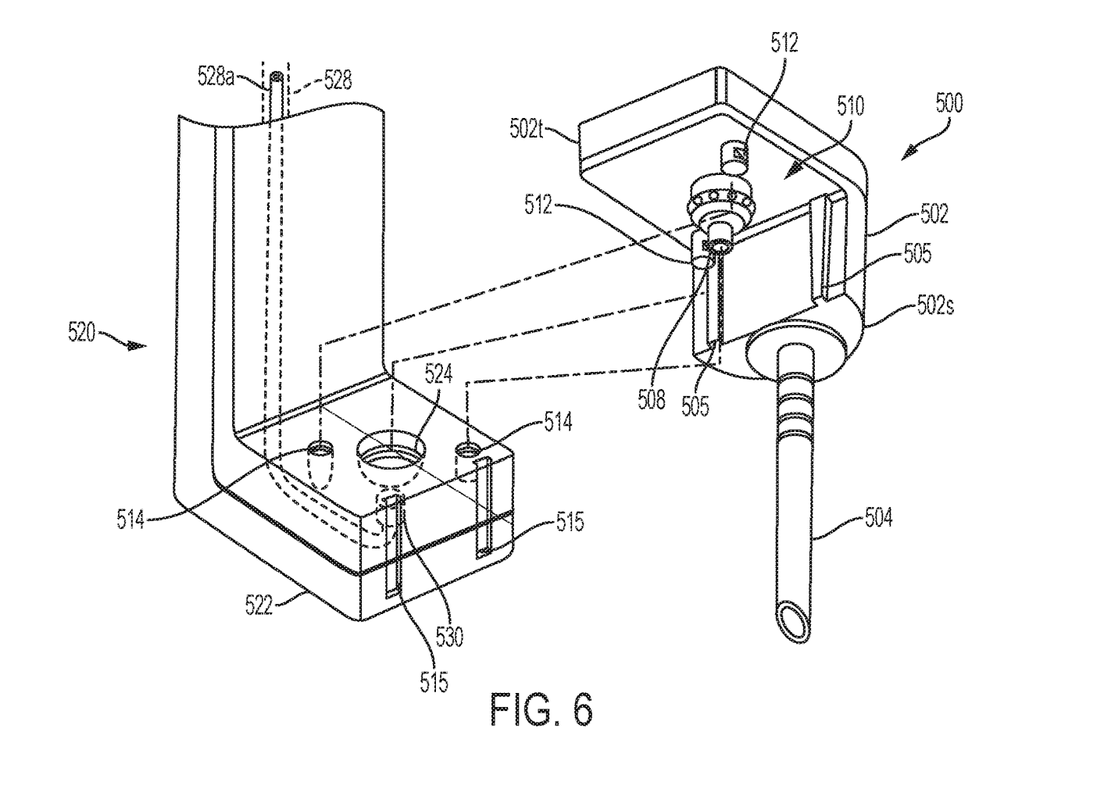
FIG. 6 is a perspective view of another embodiment of a trocar connecting to a surgical robotic arm.
Figure 7:
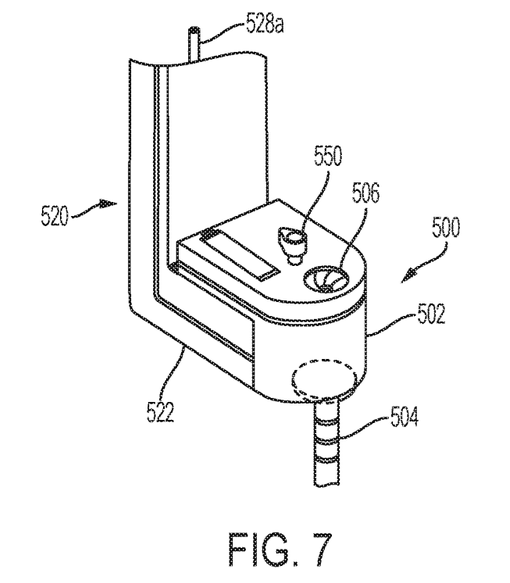
FIG. 7 is a perspective view of the trocar of FIG. 6 connected to the surgical robotic arm.
Figure 8:
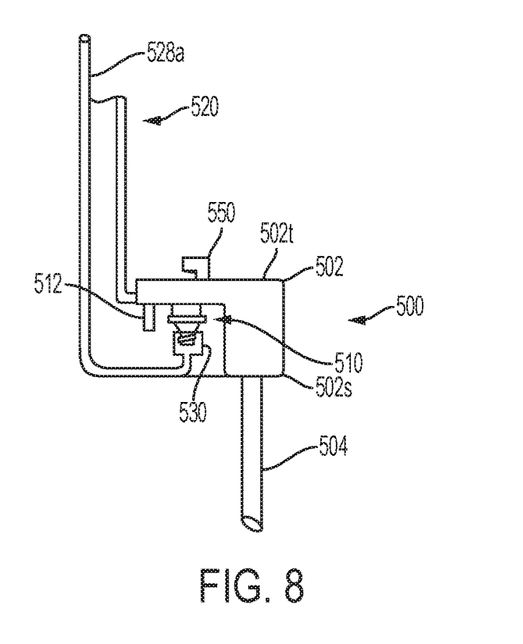
FIG. 8 is a cross-sectional view of the trocar and the surgical robotic arm of FIG. 7.

FIGS. 6-8 illustrate another embodiment of a trocar 500. As shown, the trocar 500 has a housing 502 and a cannula 504 with a tool pathway extending therethrough and having at least one seal extending thereacross, as discussed above. In this embodiment, the housing 502 has a top portion 502t and a side portion 502s that connect to one another at an approximate 90 degree angle, forming an approximate L shape. The side portion 502s is hemi-cylindrical in shape and has a flat surface formed on one side thereof and positioned underneath the top portion 502t. An opening 506 is formed on a top surface of the top portion 502t of the trocar housing 502 for receiving a surgical tool, and the tool pathway extends therethrough. As shown, an insufflation port 508 extends distally from a bottom surface of the top portion 502t and extends substantially parallel to the side portion 502s. The insufflation port 508 is part of a sealing mechanism, such as a Bal-Seal® mechanism 510, having an approximately semi-circular shape and having springs that are configured to create a seal. O-rings can be incorporated to assist in the sealing while the Bal-Seal mechanism 510 facilitates a secure but releasable connection between the trocar 500 and a carrier 520. The insufflation port 508 is in fluid communication with an insufflation pathway that extends through the top portion 502t and connects with the tool pathway so as to allow insufflation to be delivered through the cannula 504 and into a body cavity. Alignment pins 512 on the trocar housing 502 can extend distally from the bottom surface of the top portion 502t for aligning the trocar housing 502 with the trocar support, discussed below. The alignment pins 512 can extend substantially parallel to the port 508. Alignment ledges 505 can be formed along the flat surface of the side portion 502s of the housing 502 for further facilitating alignment with the trocar support.

The carrier 520 can be formed on or mounted on a distal end of a robotic arm (not shown), and the carrier 520 can include a trocar support 522 that extends therefrom such that the carrier and the trocar support are in the shape of an L. The illustrated trocar support 522 has a flat, top surface that forms a ledge. The opening 506 can include a chamfered lead-in to help guide robotic tools during installation. An opening 524 is formed in the top surface of the trocar support 522. The opening can have a shape that corresponds to the shape of the Bal-Seal mechanism 510 for seating the Bal-Seal mechanism 510 therein. An insufflation pathway 528 extends from the opening 524 through the trocar support 522, and it extends upward through the carrier 520 to mate with an insufflation source. An insufflation tubing 528a can be disposed within the insufflation pathway 528, or the pathway 528 can function to transport an insufflation fluid directly without the using of tubing 528a. A bottom of the opening 524 in the trocar support 522 can terminate at a port 530 that couples to the insufflation tubing 528a. Alignment openings 514 are formed on the top surface of the trocar support 522, and alignment grooves 515 extend along and are recessed within a front surface of the trocar support 522. In some embodiments, insufflation flow can be controlled by a flow control valve placed anywhere in line with tubing 528a. User control of the flow control value can be accomplished either manually (e.g. mechanically at the source)

and/or remotely (e.g. automatic activation) via a user interface, such as the user-side portion 106 or other user consoles.

In use, as the trocar 500 is inserted onto the trocar support 522, the top portion 502t of the trocar 500 is rested on top of the ledge-like top surface of the trocar support 522, and the flat surface of the side portion 502s of the trocar 500 rests against the front surface of the trocar support 522. The cannula 504 runs alongside the trocar support 522, as illustrated in FIGS. 7 and 8. The alignment pins 512 of the trocar 500 are inserted into the alignment openings 514 on the trocar support 522, and the alignment ledges 505 of the trocar 500 are inserted into the alignment grooves 515 of the trocar support 522 to ensure proper alignment of the trocar and to prevent or reduce radial movement. The Bal-Seal mechanism 510 of the trocar 500 is inserted into the corresponding opening 524 on the trocar support 522, forming a seal between the pathway extending through the trocar 500 and the insufflation pathway 528 extending through the support 522 and carrier 520. The port 508 on the trocar 500 engages and connects to the port 530 of the insufflation pathway 528 running through the support 522, thus allowing an insufflation fluid to be delivered therethrough and into a body cavity of a patient. As the trocar 500 is attached to the trocar support 522, the insufflation pathway is connected automatically and does not require a manual connection. A stopcock 550 can extend from an upper surface of the trocar 500, thus allow for easy access to the stopcock 550 while still maintaining a nonobtrusive design and protecting the insufflation pathway.

Figure 9:
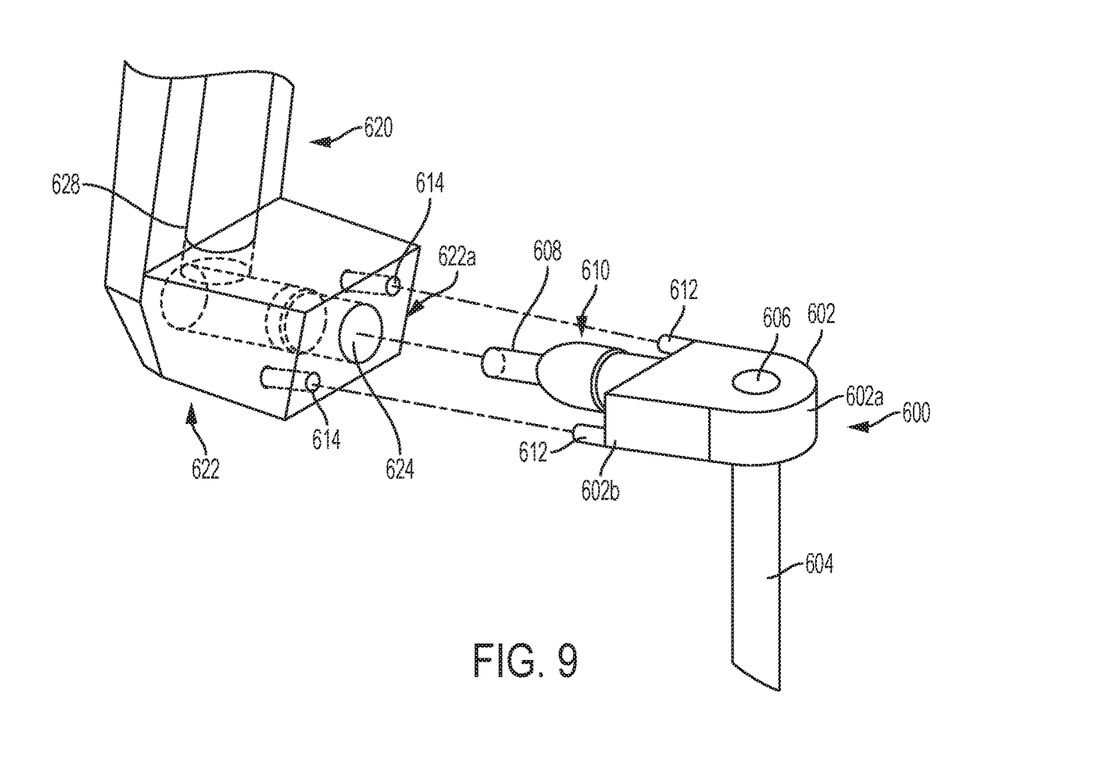
FIG. 9 is a perspective view of another embodiment of a trocar connecting to a surgical robotic arm.

Another embodiment of a trocar 600 and trocar support 622 is illustrated in FIG. 9. The trocar 600 is similar to the trocar 500 in FIGS. 6-8 and uses an O-ring or gasket to seal and Bal-Seal technology configured to facilitate a releasable mechanical connection. In various embodiments, an O-ring or gasket can be placed in front of and/or behind the Bal-Seal mechanism to create a seal. The trocar 600 has a housing 602 and a cannula 604, and a tool pathway runs therethrough with at least one seal extending thereacross. An opening 606 is formed in a top surface of the housing 602 for receiving a surgical tool. The housing 602 and the cannula 604 together are generally L-shaped, with the cannula 604 being positioned laterally outward from a center of the housing. The housing 602 has a front surface 602a and a back surface 602b. The front surface 602a has a hemicylindrical shape, and the back surface 602b is generally flat. An insufflation port 608 extends from the back surface 602b of the housing 602. The insufflation port 608 is in fluid communication with a first insufflation pathway in the form of a lumen extending through the trocar housing 602 and connecting to the tool pathway so as to allow an insufflation fluid to be delivered into a body cavity of a patient. The insufflation port 608 can include a Bal-Seal mechanism 610 that is configured with O-ring(s) and/or gasket(s) to create a releasable coupling and/or a seal when mated to the trocar support. Alignment pins 612 on the trocar housing 602 can extend from the back surface 602b of the housing 602 parallel with the port 608.

The trocar support 622 can be disposed on a distal end of a carrier 620 formed on or coupled to a robotic arm. The trocar support 622 can extend generally perpendicular to the carrier 620 to form an L shaped construct. The illustrated trocar support 622 has a front surface 622a with alignment openings 614 formed therein. A receiving opening 624 is formed on the front surface 622a, and an insufflation pathway 628 extends through the carrier 620 for receiving an insufflation tubing or for directly receiving an insufflation fluid therethrough.

As the trocar 600 is connected to the trocar support 622, the alignment pins 612 can be inserted into corresponding alignment openings 614 and the Bal-Seal mechanism 610 can be inserted into the receiving opening 624 on the trocar support 622. As the Bal-Seal mechanism 610 is inserted into the opening 624, an insufflation pathway is connected between the carrier 620 and the trocar 600.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
 a trocar defining a tool pathway extending therethrough, the trocar including at least one seal configured to seal the tool pathway and an insufflation port in fluid communication with the tool pathway and configured to deliver insufflation therethrough; and a carrier configured to be mounted to a surgical robot arm and to retain the trocar in a substantially fixed position, the carrier defining an opening configured to receive the insufflation port.

2. The surgical system of claim 1, further comprising insufflation tubing extending through the carrier and into the opening, the insufflation tubing being configured to couple with the insufflation port.

3. The surgical system of claim 1, wherein the carrier is configured to be pivotally coupled to a surgcial robot arm.

4. The surgical system of claim 1, wherein the carrier includes a pair of opposed arms configured to receive the trocar.

5. The surgical system of claim 4, wherein the pair of opposed arms are spring-biased radially inward toward each other and are configured to move radially outward to allow the trocar to be retained therebetween.

6. The surgical system of claim 2, wherein the insufflation port is substantially parallel to the tool pathway.

7. The surgical system of claim 2, wherein the insufflation port is substantially perpendicular to the tool pathway.

8. The surgical system of claim 2, wherein the insufflation port includes a B al-Seal.

9. A surgical system, comprising:
a trocar defining a tool pathway, the trocar including an insufflation port in fluid communication with the tool pathway and configured to deliver insufflation therethrough;

a trocar holder configured to mount to a surgical arm at a first end and configured to retain the trocar at a second end, the trocar holder defining a fluid pathway therethrough; and wherein the fluid pathway and the tool pathway are in fluid communication via the insufflation port when the trocar is retained within the trocar holder.

10. The surgical system of claim 9, wherein the tool pathway and the insufflation port are substantially parallel to each other.

11. The surgical system of claim 9, wherein the tool pathway and the insufflation port are substantially perpendicular to each other.

12. The surgical system of claim 9, wherein the tool pathway is configured to receive and retain a surgical tool, and wherein the trocar includes at least one seal configured to seal around a retained surgical tool.

13. The surgical system of claim 12, wherein the at least one seal is configured to seal the tool pathway when a surgical tool is not retained therein.

* * * * *